(12) United States Patent
Markovitz et al.

(10) Patent No.: US 10,610,120 B2
(45) Date of Patent: Apr. 7, 2020

(54) SYSTEM AND METHOD FOR GENERATING PREMATURE VENTRICULAR CONTRACTION ELECTROPHYSIOLOGY MAPS

(71) Applicant: St. Jude Medical, Cardiology Division, Inc., St. Paul, MN (US)

(72) Inventors: Craig Markovitz, Leipzig (DE); Stuart Rosenberg, Castaic, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 112 days.

(21) Appl. No.: 15/868,051

(22) Filed: Jan. 11, 2018

(65) Prior Publication Data

US 2018/0199847 A1 Jul. 19, 2018

Related U.S. Application Data

(60) Provisional application No. 62/446,039, filed on Jan. 13, 2017.

(51) Int. Cl.
| | |
|---|---|
| A61B 5/0452 | (2006.01) |
| A61B 5/044 | (2006.01) |
| A61B 5/04 | (2006.01) |
| A61B 5/02 | (2006.01) |
| A61B 5/046 | (2006.01) |
| A61B 5/00 | (2006.01) |

(52) U.S. Cl.
CPC ...... *A61B 5/04525* (2013.01); *A61B 5/02028* (2013.01); *A61B 5/044* (2013.01); *A61B 5/046* (2013.01); *A61B 5/04012* (2013.01); *A61B 5/7246* (2013.01); *A61B 5/7264* (2013.01)

(58) Field of Classification Search
CPC .............. A61B 5/04525; A61B 5/02028
USPC .............................................. 600/515
See application file for complete search history.

(56) References Cited

U.S. PATENT DOCUMENTS

| | | |
|---|---|---|
| 5,697,377 A | 12/1997 | Wittkampf |
| 5,983,126 A | 11/1999 | Wittkampf |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |

(Continued)

*Primary Examiner* — Nadia A Mahmood
(74) *Attorney, Agent, or Firm* — Wiley Rein LLP

(57) ABSTRACT

A method of mapping arrhythmic activity, such as premature ventricular contraction ("PVC") activity, using an electroanatomical mapping system includes defining at least two arrhythmia template signals. Electrophysiology data points, each including an electrophysiological signal, are collected. A morphological similarity between the electrophysiological signal and a first arrhythmia template signal is computed; if this exceeds a preset threshold, then the electrophysiology data point is added to a corresponding arrhythmia map. If it does not, a morphological similarity between the electrophysiological signal and a second arrhythmia template signal is computed. If this exceeds the preset threshold, then the electrophysiology data point is added to a corresponding arrhythmia map. If neither exceeds the preset threshold, then the electrophysiology data point can be used to establish an additional arrhythmia map by defining an additional arrhythmia template signal.

19 Claims, 3 Drawing Sheets

(56) References Cited

U.S. PATENT DOCUMENTS

| | | |
|---|---|---|
| 6,990,370 B1 | 1/2006 | Beatty et al. |
| 7,263,397 B2 | 8/2007 | Hauck et al. |
| 7,885,707 B2 | 2/2011 | Hauck |
| 2015/0057507 A1* | 2/2015 | Koyrakh ................ A61B 5/066 |
| | | 600/301 |
| 2017/0086700 A1 | 3/2017 | Stewart et al. |
| 2017/0086701 A1 | 3/2017 | Stewart et al. |

* cited by examiner

SYSTEM AND METHOD FOR GENERATING PREMATURE VENTRICULAR CONTRACTION ELECTROPHYSIOLOGY MAPS

CROSS-REFERENCE TO RELATED APPLICATIONS

This application claims the benefit of U.S. provisional application No. 62/446,039, filed 13 Jan. 2017, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for generating electrophysiology maps that include multiple premature ventricular contraction morphologies.

Electrophysiological mapping, and more particularly electrocardiographic mapping, is a part of numerous cardiac and diagnostic and therapeutic procedures. As the complexity of such procedures increases, however, the electrophysiology maps utilized must increase in quality, in density, and in the rapidity and ease with which they can be generated.

Some of the most time consuming electrophysiology procedures involve mapping ventricular tachycardia ("VT") and/or incessant premature ventricular contractions ("PVC"), particularly where the clinical morphology presents infrequently during a procedure. In these procedures, the physician can be required to wait at each map point for a PVC to occur in order to collect the point. The task becomes even more time consuming if multiple PVC morphologies are being mapped.

BRIEF SUMMARY

Disclosed herein is a method of mapping arrhythmic activity using an electroanatomical mapping system, including: defining at least two arrhythmia template signals, the at least two arrhythmia template signals including a first arrhythmia template signal associated with a first arrhythmia map and a second arrhythmia template signal associated with a second arrhythmia map; collecting an electrophysiology data point, wherein the electrophysiology data point includes an electrophysiological signal; computing a first morphological similarity between the electrophysiological signal and the first arrhythmia template signal; if the first morphological similarity exceeds a preset threshold: adding the electrophysiology data point to the first arrhythmia map; if the first morphological similarity does not exceed the preset threshold: computing a second morphological similarity between the electrophysiological signal and the second arrhythmia template signal; and if the first morphological similarity does not exceed the threshold and the second morphological similarity exceeds the preset threshold: adding the electrophysiology data point to the second arrhythmia map.

The method can also include, if the first morphological similarity does not exceed the preset threshold and the second morphological similarity does not exceed the preset threshold: defining the electrophysiological signal as a third arrhythmia template signal of the at least two arrhythmia template signals, wherein the third arrhythmia template signal is associated with a third arrhythmia map; and adding the electrophysiology data point to the third arrhythmia map.

In additional embodiments, the method can include, if the first morphological similarity does not exceed the preset threshold and the second morphological similarity does not exceed the preset threshold: computing a third morphological similarity between the electrophysiological signal and an unwanted signal; and rejecting the electrophysiology data point from inclusion any arrhythmia map if the third morphological similarity exceeds the preset threshold.

The preset threshold can be between about 0.55 and about 1.00, such as about 0.85.

It is contemplated that the method can include: outputting a graphical representation the first arrhythmia map on a three dimensional cardiac model if the first arrhythmia map includes more than a preset number of electrophysiology data points; and outputting a graphical representation of the second arrhythmia map on the three dimensional model cardiac model if the second arrhythmia map includes more than the preset number of electrophysiology data points.

In addition, if the second arrhythmia map includes more electrophysiology data points than the first arrhythmia map, then the method can include: redefining the second arrhythmia template signal as the first arrhythmia template signal; redefining the first arrhythmia template signal as the second arrhythmia template signal; redefining the second arrhythmia map as the first arrhythmia map; and redefining the first arrhythmia map as the second arrhythmia map.

According to aspects of the disclosure, the step of defining at least two arrhythmia template signals includes: receiving, in the electroanatomical mapping system, user input selecting a first electrophysiology data point including a first electrophysiological signal and a second electrophysiology data point including a second electrophysiological signal; defining the first electrophysiological signal as the first arrhythmia template signal; adding the first electrophysiology data point to the first arrhythmia map; defining the second electrophysiological signal as the second arrhythmia template signal; and adding the second electrophysiology data point to the second arrhythmia map.

In other aspects of the disclosure, the step of defining at least two arrhythmia template signals includes: collecting a first electrophysiology data point including a first electrophysiological signal; defining the electrophysiological signal as the first arrhythmia template signal; adding the first electrophysiology data point to the first arrhythmia map; collecting a second electrophysiology data point including a second electrophysiological signal, wherein a morphological similarity between the second electrophysiological signal and the first electrophysiological signal does not exceed the preset threshold; defining the second electrophysiological signal as the second arrhythmia template signal; and adding the second electrophysiology data point to the second arrhythmia map.

The at least two arrhythmia template signals can include least two EKG signals and/or at least two electrogram signals. At least one of the at least two arrhythmia template signals can also include a premature ventricular contraction ("PVC") template signal.

Also disclosed herein is a method of mapping premature ventricular contraction ("PVC") activity using an electroanatomical mapping system, including: establishing a plurality of PVC maps, each PVC map of the plurality of PVC maps having an associated PVC template signal; collecting an electrophysiology data point including an electrophysiological signal; sequentially comparing the electrophysiological signal to the PVC template signal associated with a PVC map until a first to occur of: a morphological similarity between the electrophysiological signal and the PVC template signal exceeds a preset threshold; or the electrophysiological signal has been compared to each PVC template signal of each PVC map without the morphological similarity between the electrophysiological signal and the PVC template signal exceeding the preset threshold; and if the first to occur is the morphological similarity between the electrophysiological signal and the PVC template signal exceeds the preset threshold: adding the electrophysiology data point to the PVC map associated with the PVC template signal.

It is contemplated that the sequence in which the electrophysiological signal is sequentially compared to PVC template signals associated with the plurality of PVC maps corresponds to a diminishing number of electrophysiology data points in the plurality of PVC maps.

In embodiments of the disclosure, if the first to occur is the electrophysiological signal has been compared to each PVC template signal of each PVC map without the morphological similarity between the electrophysiological signal and the PVC template signal exceeding the preset threshold, then the method includes: computing a morphological similarity between the electrophysiological signal and an unwanted signal; and if the morphological similarity between the electrophysiological signal and the unwanted signal does not exceed the preset threshold: defining an additional PVC map having the electrophysiological signal as its associated PVC template signal.

The method can include repeating the steps of collecting an electrophysiology data point including an electrophysiological signal; sequentially comparing the electrophysiological signal to the PVC template signal associated with a PVC map until a first to occur of: a morphological similarity between the electrophysiological signal and the PVC template signal exceeds a preset threshold; or the electrophysiological signal has been compared to each PVC template signal of each PVC map without the morphological similarity between the electrophysiological signal and the PVC template signal exceeding the preset threshold; if the first to occur is the morphological similarity between the electrophysiological signal and the PVC template signal exceeds the preset threshold: adding the electrophysiology data point to the PVC map associated with the PVC template signal; and if the first to occur is the electrophysiological signal has been compared to each PVC template signal of each PVC map without the morphological similarity between the electrophysiological signal and the PVC template signal exceeding the preset threshold: computing a morphological similarity between the electrophysiological signal and an unwanted signal; and if the morphological similarity between the electrophysiological signal and the unwanted signal does not exceed the preset threshold: defining an additional PVC map having the electrophysiological signal as its associated PVC template signal, a plurality of times, such that each PVC map of the plurality of PVC maps includes at least one electrophysiology data point. Any PVC map of the plurality of PVC maps that includes fewer than a preset number of electrophysiology data points can then be discarded.

The step of establishing a plurality of PVC maps, each PVC map of the plurality of PVC maps having an associated PVC template signal, can include: receiving, in the electroanatomical mapping system, user input selecting a plurality of electrophysiology data points, each selected electrophysiology data point including an associated electrophysiological signal; and establishing a PVC map for each selected electrophysiology data point, wherein the PVC map includes the respective selected electrophysiology data point, and wherein the template signal associated with the PVC map is the electrophysiological signal associated with the respective selected electrophysiology data point.

In other embodiments, the step of establishing a plurality of PVC maps, each PVC map of the plurality of PVC maps having an associated PVC template signal, can include: collecting a plurality of electrophysiology data points using the electroanatomical mapping system; identifying a plurality of distinct electrophysiological signal morphologies within the plurality of electrophysiology data points; and establishing the plurality of PVC maps using the plurality of distinct electrophysiological signal morphologies.

According to further aspects of the disclosure, the method can also include merging two or more PVC maps of the plurality of PVC maps into a consolidated PVC map and/or outputting a graphical representation at least one PVC map of the plurality of PVC maps on a three dimensional cardiac model.

In still further embodiments, the instant disclosure provides a system for mapping premature ventricular contraction ("PVC") activity, including: a PVC comparison processor configured to: compute morphological similarities between an electrophysiological signal associated with an electrophysiology data point and a plurality of PVC template signals; and add the electrophysiology data point to a PVC map based upon the computed morphological similarities; and a mapping processor configured to generate a graphical representation of the at least one PVC map on a three dimensional cardiac model.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure provides methods, apparatuses, and systems for the creation of electrophysiology maps (e.g., electrocardiographic maps) using an electrophysiology mapping system (e.g., using a electroanatomical mapping system such as the EnSite Precision™ cardiac mapping system from St. Jude Medical). For purposes of illustration, several exemplary embodiments will be described in detail herein in the context of a cardiac electrophysiology procedure related to the creation of maps of PVC activity. It is contemplated, however, that the methods, apparatuses, and systems described herein can be utilized in other contexts, including, but not limited to, atrial electrophysiology mapping. For example, the teachings herein can be applied to good advantage when mapping the left atrium of a patient that fluctuates between sinus rhythm and atrial fibrillation.

Figure 1:
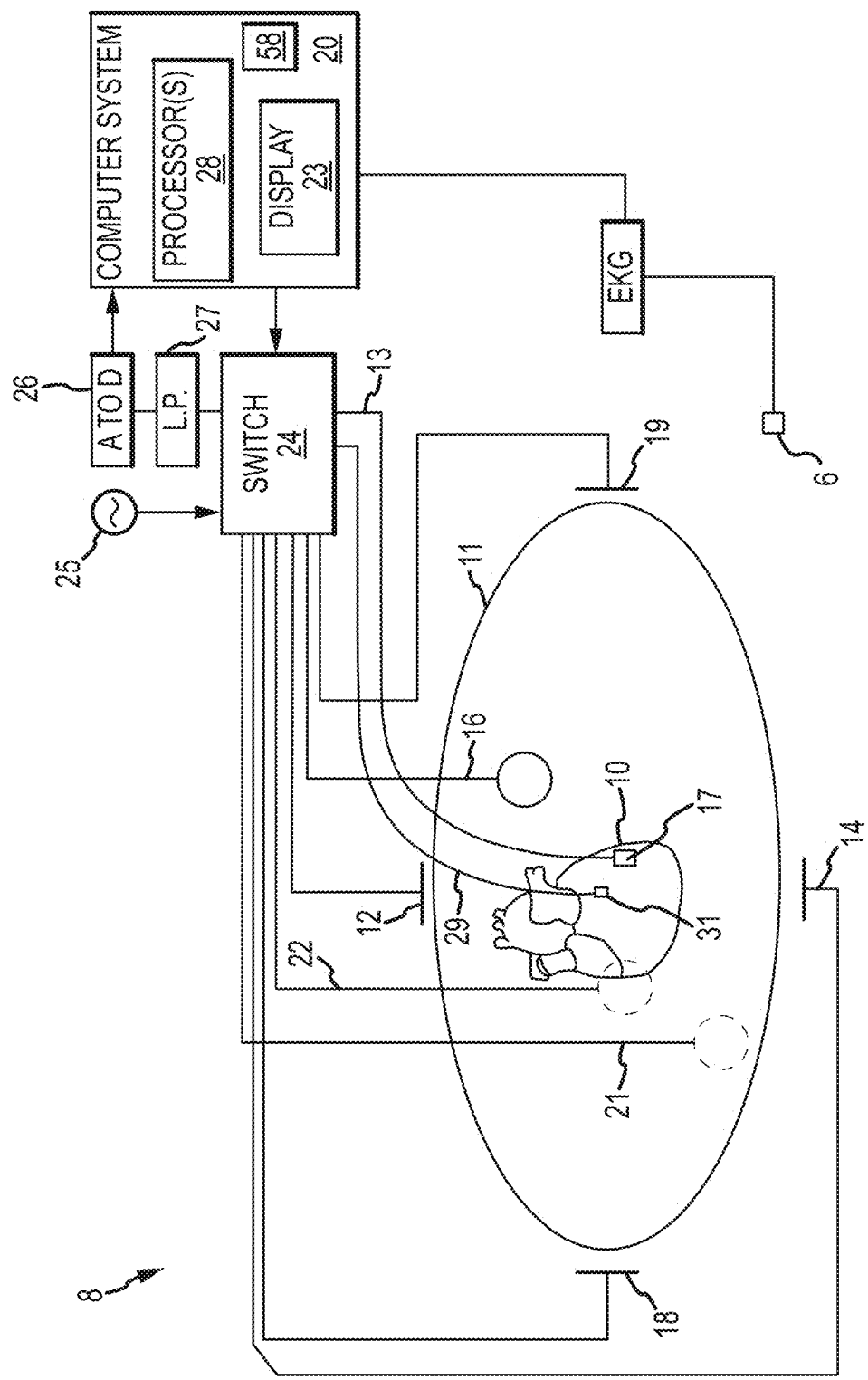
FIG. 1 is a schematic diagram of an exemplary electroanatomical mapping system.

FIG. 1 shows a schematic diagram of an exemplary system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10. In some embodiments, and as discussed further herein, the system 8 can be used to generate electrophysiology maps of PVC activity. In some embodiments, for example, the system 8 includes various software and hardware functionality to aid in detecting and classifying PVC activity.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 its connection to computer 20 is illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
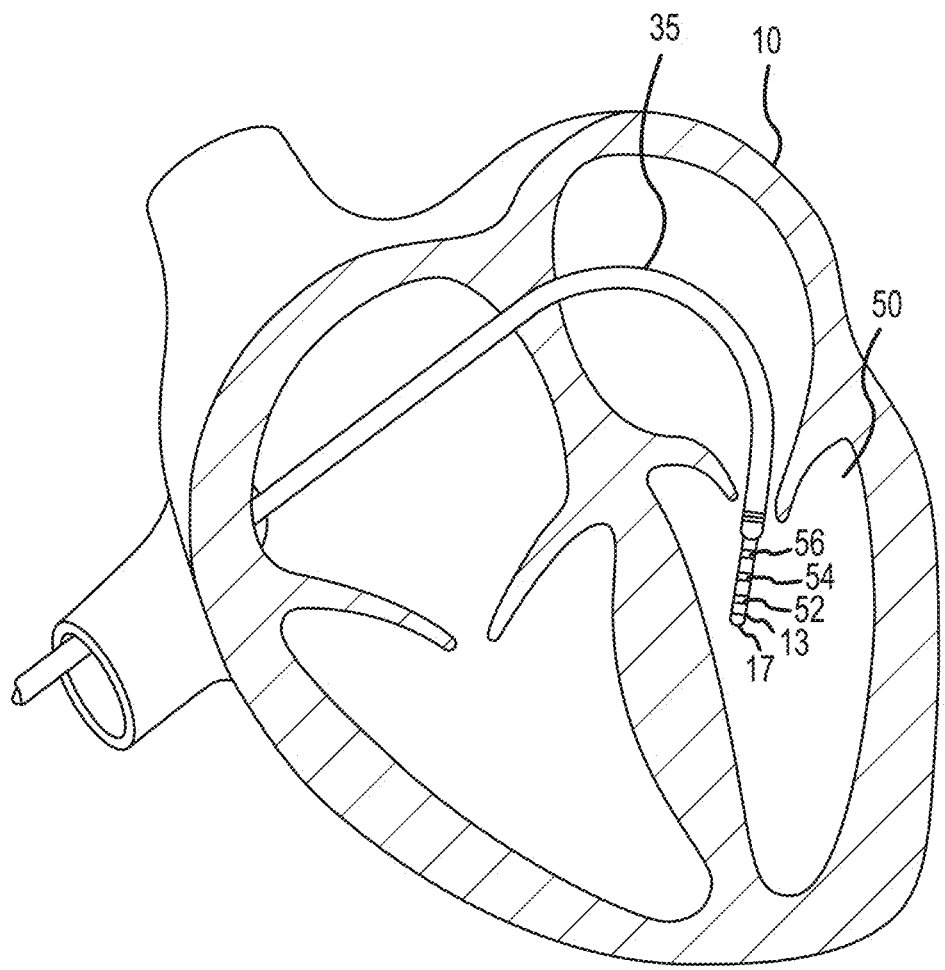
FIG. 2 depicts an exemplary catheter that can be used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three)

instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of St. Jude Medical, Inc. Other localization systems, however, may be used in connection with the present teachings, including for example the CARTO navigation and location system of Biosense Webster, Inc., the AURORA® system of Northern Digital Inc., Sterotaxis' NIOBE® Magnetic Navigation System, as well as MediGuide™ Technology from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to the creation of PVC maps. The system 8 can therefore also include an arrhythmias module 58 that can be used to analyze electrograms for arrhythmic activity of interest (e.g., PVC activity) and to classify electrograms based on their morphology. Based on this analysis and classification, and as discussed further herein, maps of various arrhythmias, including without limitation PVC maps, can be generated.

A PVC map is a type of electrophysiology map. Those of ordinary skill in the art will appreciate that electrophysiology maps, including, but not limited to, PVC maps, include a plurality of electrophysiology data points, and that each electrophysiology data point in turn includes both measured electrophysiology data (e.g., an electrophysiological signal, such as a cardiac electrogram ("EGM")) and location data (e.g., information regarding the location of catheter 13 and/or electrodes 17, 52, 54, 56 thereon), allowing the measured electrophysiology information to be associated with a particular location in space (that is, allowing the measured electrophysiology information to be interpreted as indicative of electrical activity at a point on the patient's heart).

Those of ordinary skill in the art will also be familiar with various aspects of the collection of electrophysiology data points and the creation of electrophysiology maps therefrom. By way of example only, however, United States patent application publication no. 2015/0057507, which is hereby incorporated by reference as though fully set forth herein, describes various methods and systems for the collection of electrophysiology data points and the creation of electrophysiology maps to which the teachings of the instant disclosure can be applied.

One exemplary method for mapping PVC activity according to the present teachings will be explained with reference to the flowchart 300 of representative steps presented as FIG. 3. In some embodiments, for example, flowchart 300 may represent several exemplary steps that can be carried out by the computer 20 of FIG. 1 (e.g., by processor 28, including arrhythmia module 58). It should be understood that the representative steps described below can be either hardware- or software-implemented. For the sake of explanation, the term "signal processor" is used herein to describe both hardware- and software-based implementations of the teachings herein.

In block 302, a first PVC template signal is defined and associated with a first PVC map. As used herein, a "PVC template signal" is an electrophysiology signal possessing a morphology (a "PVC template morphology") that is of interest to a practitioner in a particular electrophysiology study (e.g., when mapping PVC activity). In particular, the first PVC template signal is defined as the electrophysiological signal associated with a collected electrophysiology data point, which electrophysiology data point is then added to the first PVC map.

Various approaches to identifying the electrophysiology data point that will be used to define the first PVC template signal and establish the first PVC map are contemplated. According to aspects of the disclosure, it is an electrophysiology data point that is manually collected by the practitioner, such as by clicking a "freeze and save" button on a graphical user interface. According to other aspects of the disclosure, it is the first electrophysiology data point that is collected as catheter 13 roves that satisfies one or more user-defined, non-morphological inclusion criteria. The use of inclusion criteria (both morphological and non-morphological) in the creation of electrophysiology maps is described, for example, in United States patent application publication no. 2015/0057507.

A second PVC template signal is defined and associated with a second PVC map in block 304. Analogous to the first PVC template signal, the second PVC template signal is defined as the electrophysiological signal associated with a collected electrophysiology data point, which electrophysiology data point can also be added to the second PVC map.

Various approaches to identifying the electrophysiology data point that will be used to define the second PVC template signal and establish the second PVC map are contemplated. According to aspects of the disclosure, it is an electrophysiology data point that is manually selected by the practitioner, such as by clicking a "new map" button on a graphical user interface, and can be so selected if the practitioner considers it to exhibit a different morphology of interest as compared to the first PVC template signal.

In other aspects of the disclosure, the electrophysiology data point that is used to define the second PVC template signal and establish the second PVC map is automatically identified by system 8 (e.g., by arrhythmia module 58), for example when analysis establishes that the morphology of the electrophysiological signal associated with a collected electrophysiology data point is sufficiently dissimilar from the morphology of the first PVC template signal. This will be described in further detail below.

The PVC template signals described above can be surface ECG signals and/or intracardiac EGM signals. In embodiments where the PVC template signal includes a surface ECG component, it is desirable to use the signal from more than one (e.g., between two and six) ECG leads (e.g., leads I, aVF, V2, and V5). This facilitates discrimination among activation sequences originating from different foci.

In block 306, an electrophysiology data point is collected (e.g., using electrodes 17, 52, 54, and/or 56 on catheter 13). If inclusion criteria are in use, the collected electrophysiology data point can be discarded if it does not satisfy the inclusion criteria, for example as disclosed in United States patent application publication no. 2015/0057507. For purposes of this disclosure, however, it will be assumed that the collected electrophysiology data point satisfies any applicable non-morphological inclusion criteria.

Beginning in block 308, the electrophysiological signal of the collected electrophysiology data point is sequentially compared to PVC template signals (e.g., first and second PVC template signals defined in blocks 302 and 304, respectively) to compute morphological similarities therebetween. Each computed morphological similarity is compared to a preset threshold to determine to which PVC map, if any, the collected electrophysiology data point should be added.

Various techniques for computing morphological similarities for purposes of carrying out morphology comparisons are regarded as within the scope of the instant disclosure. These techniques generally include computing morphology matching scores between the electrophysiological signal of the collected electrophysiology data point, on the one hand, and a PVC template signal, on the other hand. A higher matching score indicates a higher degree of similarity. According to aspects of the disclosure, the preset threshold is about 0.85, though suitable thresholds range from about 0.55 to about 1.00.

Several approaches to computing matching scores are described in United States patent application publication no. 2015/0057507, which is incorporated by reference above. For the sake of convenience of the reader, however, certain of these techniques are also expressly described below.

In one aspect, a matching score can be calculated as follows. First, a distance can be computed between the PVC template signal, on the one hand, and a zero signal, on the other hand. This distance is referred herein to as a "template area."

Next, a distance is computed between the electrophysiological signal of the collected electrophysiology data point, on the one hand, and the PVC template signal, on the other hand. This distance can then be divided by the template area. The resulting ratio can be subtracted from one and expressed as a percentage matching score; if the ratio is greater than one, a 0% matching score is assigned. As discussed above, a higher matching score corresponds to a higher degree of morphological similarity between the two signals.

In other embodiments of the disclosure, the Pearson Correlation Coefficient can be used as an alternative or in addition to a distance function in order to compute a morphology matching score. For example, a score S can be computed according to the equation $S=P*f(r)$, where: (1) P is the Pearson Correlation Coefficient of the PVC template signal, on the one hand, and the electrophysiological signal of the collected electrophysiology data point, on the other hand; (2) r is the ratio of amplitudes of the PVC template signal, on the one hand, and the electrophysiological signal of the collected electrophysiology data point, on the other hand and is defined such that $0 \le r \le 1$ (e.g., the larger amplitude is in the denominator when computing r); and (3) $f(r)$ is a monotonically increasing function with output in the range $0 \le f(r) \le 1$. Signal amplitudes can be measured by, for example, the standard deviation or peak-to-peak measurement.

In decision block 308, system 8 (e.g., arrhythmia module 58) computes a first morphological similarity, between the electrophysiological signal of the collected electrophysiology data point and the first PVC template signal, and compares it to the preset threshold. If the first morphological similarity exceeds the preset threshold, then the collected electrophysiology data point collected is added to the first PVC map ("YES" exit from decision block 308 to block 310). The process then returns to block 306 to collect a new electrophysiology data point.

If the first morphological similarity does not exceed the preset threshold ("NO" exit from decision block 308), then system 8 (e.g., arrhythmia module 58) computes a second morphological similarity, between the electrophysiological signal of the collected electrophysiology data point and the second PVC template signal, and compares it to the preset threshold in decision block 312. If the second morphological similarity exceeds the preset threshold, then the collected electrophysiology data point is added to the second PVC map ("NO" exit from decision block 312 to block 314). The process then returns to block 306 to collect a new electrophysiology data point.

It is computationally advantageous for the electrophysiological signal of the collected electrophysiology data point to be compared first to the PVC template signal associated with the PVC map having the most electrophysiology data points, next to the PVC template signal associated with the PVC map having the second most electrophysiology data points, and so on until it is finally compared to the PVC template signal associated with the PVC map having the fewest electrophysiology data points. In other words, decision blocks 308 and 312 (and any similar decision blocks for additional PVC template signals defined in accordance with the teachings herein) are desirably sequenced according to a diminishing number of electrophysiology data points in the respective PVC maps.

For example, and with reference to the two PVC template signals and associated maps described above, when the second PVC map includes more electrophysiology data points than the first PVC map, the first and second PVC template signals and PVC maps are reversed. That is, the second PVC template signal is redefined as the first PVC template signal and vice versa and the second PVC map is redefined as the first PVC map and vice versa. It should be understood that this resequencing of PVC template signals and their associated maps can occur as many times as necessary, and with respect to as many PVC template signals/PVC maps as present, throughout an electrophysiology study.

In additional aspects, the instant disclosure relates to the automatic rejection or exclusion of electrophysiology data points based on their morphology being sufficiently similar to an unwanted signal and dissimilar to any previously-defined PVC template signal. An "unwanted signal" is defined as an electrophysiological signal possessing a morphology (an "unwanted morphology") that is not of interest to a practitioner in a particular electrophysiology study. For example, in aspects of the instant disclosure, the unwanted signal is a signal with QS morphology, which can result from catheter 13 mechanically inducing PVC.

Figure 3:
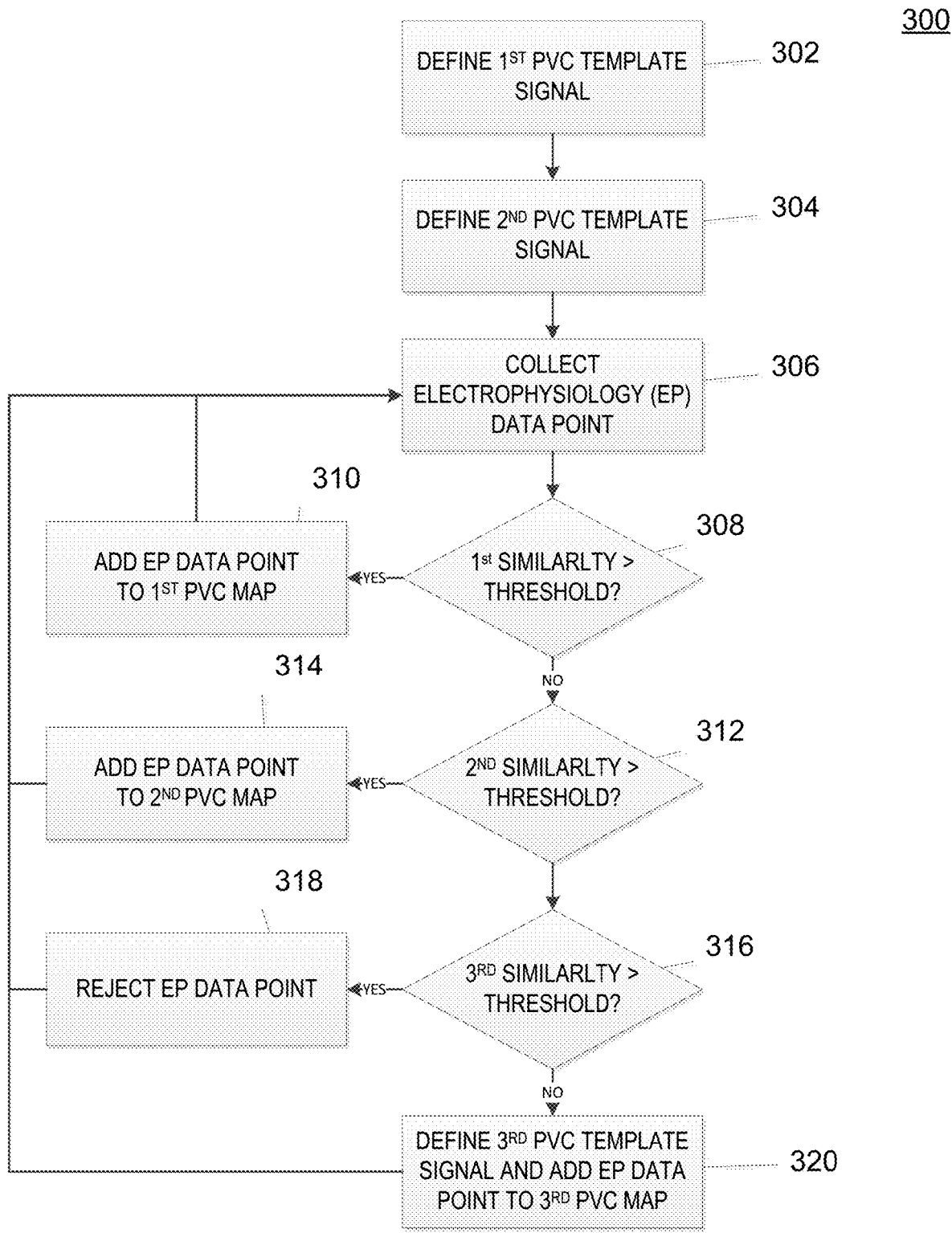
FIG. 3 is a flowchart of representative steps that can be followed according to exemplary embodiments disclosed herein.

One suitable approach to the automatic rejection or exclusion of electrophysiology data points, which is summarized herein with reference to FIG. 3, is disclosed in greater detail in U.S. provisional application No. 62/420,811, filed 11 Nov. 2016, which is hereby incorporated by reference as though fully set forth herein.

In particular, if the second morphological similarity also does not exceed the preset threshold ("NO" exit from decision block 312), then system 8 (e.g., arrhythmia module 58) can proceed to decision block 316. In decision block 316, a third morphological similarity is computed, between the electrophysiological signal of the collected electrophysiology data point and the unwanted signal, and is compared to the preset threshold. If the third morphological similarity exceeds the preset threshold ("YES" exit from decision block 316), then the collected electrophysiology data point is discarded in block 318 and the process returns to block 306 to collect an additional electrophysiology data point.

If, on the other hand, the third morphological similarity does not exceed the preset threshold ("NO" exit from decision block 316), then system 8 (e.g., arrhythmia module 58) can use the collected electrophysiology data point to define a new (e.g., third) PVC template signal and establish a new (e.g., third) PVC map, including the collected electrophysiology data point, in block 320. The process then returns to block 306 to collect a new electrophysiology data point.

By repeating the process described above for a plurality of collected electrophysiology data points, a plurality of PVC maps, each populated with one or more electrophysiology data points, will be established. Any PVC map that is populated by fewer than a preset number of points (e.g., fewer than three points) can be discarded. This helps facilitate the elimination of PVC maps that reflect non-clinical factors, such as contact between catheter 13 and the endocardium.

As an alternative or in addition to discarding certain PVC maps, the practitioner can choose to merge two or more PVC maps into a consolidated PVC map. For example, if the practitioner manually defined two or more template PVC signals believing them to have distinct morphologies, but later determines that they are not distinct morphologies, those two PVC maps could be consolidated into one.

Any or all of the remaining PVC maps can then be graphically represented on a three dimensional cardiac model.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, although embodiments including three template PVC signals and three PVC maps are described above, any number of PVC template signals can be defined, and thus any number of corresponding PVC maps can be established, depending, for example, on the number of dissimilar PVC morphologies detected by system 8 (e.g., by Arrhythmia module 58) during an electrophysiology study and/or of interest to (e.g., manually selected by) the practitioner.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping arrhythmic activity using an electroanatomical mapping system, comprising:
   defining at least two arrhythmia template signals, the at least two arrhythmia template signals comprising a first arrhythmia template signal associated with a first arrhythmia map and a second arrhythmia template signal associated with a second arrhythmia map, wherein at least one of the at least two arrhythmia template signals comprises a premature ventricular contraction ("PVC") template signal;
   collecting an electrophysiology data point, wherein the electrophysiology data point includes an electrophysiological signal;
   computing a first morphological similarity between the electrophysiological signal and the first arrhythmia template signal;
   if the first morphological similarity exceeds a preset threshold:
      adding the electrophysiology data point to the first arrhythmia map;
   if the first morphological similarity does not exceed the preset threshold:
      computing a second morphological similarity between the electrophysiological signal and the second arrhythmia template signal; and
   if the first morphological similarity does not exceed the threshold and the second morphological similarity exceeds the preset threshold:
      adding the electrophysiology data point to the second arrhythmia map.

2. The method according to claim 1, further comprising, if the first morphological similarity does not exceed the preset threshold and the second morphological similarity does not exceed the preset threshold:
   defining the electrophysiological signal as a third arrhythmia template signal of the at least two arrhythmia template signals, wherein the third arrhythmia template signal is associated with a third arrhythmia map; and
   adding the electrophysiology data point to the third arrhythmia map.

3. The method according to claim 1, wherein the preset threshold is between 0.55 and 1.00.

4. The method according to claim 3, wherein the preset threshold is 0.85.

5. The method according to claim 1, further comprising:
   outputting a graphical representation the first arrhythmia map on a three dimensional cardiac model if the first arrhythmia map includes more than a preset number of electrophysiology data points; and
   outputting a graphical representation of the second arrhythmia map on the three dimensional model cardiac model if the second arrhythmia map includes more than the preset number of electrophysiology data points.

6. The method according to claim 1, further comprising, if the second arrhythmia map includes more electrophysiology data points than the first arrhythmia map:
   redefining the second arrhythmia template signal as the first arrhythmia template signal;
   redefining the first arrhythmia template signal as the second arrhythmia template signal;
   redefining the second arrhythmia map as the first arrhythmia map; and
   redefining the first arrhythmia map as the second arrhythmia map.

7. The method according to claim 1, wherein defining at least two arrhythmia template signals comprises:
   receiving, in the electroanatomical mapping system, user input selecting a first electrophysiology data point including a first electrophysiological signal and a second electrophysiology data point including a second electrophysiological signal;
   defining the first electrophysiological signal as the first arrhythmia template signal;
   adding the first electrophysiology data point to the first arrhythmia map;
   defining the second electrophysiological signal as the second arrhythmia template signal; and
   adding the second electrophysiology data point to the second arrhythmia map.

8. The method according to claim 1, wherein defining at least two arrhythmia template signals comprises:
   collecting a first electrophysiology data point including a first electrophysiological signal;
   defining the electrophysiological signal as the first arrhythmia template signal;
   adding the first electrophysiology data point to the first arrhythmia map;
   collecting a second electrophysiology data point including a second electrophysiological signal, wherein a morphological similarity between the second electrophysiological signal and the first electrophysiological signal does not exceed the preset threshold;
   defining the second electrophysiological signal as the second arrhythmia template signal; and
   adding the second electrophysiology data point to the second arrhythmia map.

9. The method according to claim 1, wherein the at least two arrhythmia template signals comprise at least two EKG signals.

10. The method according to claim 1, wherein the at least two arrhythmia template signals comprise at least two electrogram signals.

11. A method of mapping premature ventricular contraction ("PVC") activity using an electroanatomical mapping system, comprising:
   establishing a plurality of PVC maps, each PVC map of the plurality of PVC maps having an associated PVC template signal;
   collecting an electrophysiology data point including an electrophysiological signal;
   sequentially comparing the electrophysiological signal to the PVC template signal associated with a PVC map, wherein the sequence in which the electrophysiological signal is sequentially compared to PVC template signals associated with the plurality of PVC maps occurs corresponds to a diminishing number of electrophysiology data points in the plurality of PVC maps, until a first to occur of:
      a morphological similarity between the electrophysiological signal and the PVC template signal exceeds a preset threshold; or
      the electrophysiological signal has been compared to each PVC template signal of each PVC map without the morphological similarity between the electrophysiological signal and the PVC template signal exceeding the preset threshold; and
   if the first to occur is the morphological similarity between the electrophysiological signal and the PVC template signal exceeds the preset threshold:
      adding the electrophysiology data point to the PVC map associated with the PVC template signal.

12. The method according to claim 11, further comprising, if the first to occur is the electrophysiological signal has been compared to each PVC template signal of each PVC map without the morphological similarity between the electrophysiological signal and the PVC template signal exceeding the preset threshold:
  computing a morphological similarity between the electrophysiological signal and an unwanted signal; and
  if the morphological similarity between the electrophysiological signal and the unwanted signal does not exceed the preset threshold:
    defining an additional PVC map having the electrophysiological signal as its associated PVC template signal.

13. The method according to claim 12, further comprising repeating:
  collecting an electrophysiology data point including an electrophysiological signal;
  sequentially comparing the electrophysiological signal to the PVC template signal associated with a PVC map until a first to occur of:
    a morphological similarity between the electrophysiological signal and the PVC template signal exceeds a preset threshold; or
    the electrophysiological signal has been compared to each PVC template signal of each PVC map without the morphological similarity between the electrophysiological signal and the PVC template signal exceeding the preset threshold;
  if the first to occur is the morphological similarity between the electrophysiological signal and the PVC template signal exceeds the preset threshold:
    adding the electrophysiology data point to the PVC map associated with the PVC template signal; and
  if the first to occur is the electrophysiological signal has been compared to each PVC template signal of each PVC map without the morphological similarity between the electrophysiological signal and the PVC template signal exceeding the preset threshold:
    computing a morphological similarity between the electrophysiological signal and an unwanted signal; and
    if the morphological similarity between the electrophysiological signal and the unwanted signal does not exceed the preset threshold:
      defining an additional PVC map having the electrophysiological signal as its associated PVC template signal,
a plurality of times, such that each PVC map of the plurality of PVC maps includes at least one electrophysiology data point.

14. The method according to claim 13, further comprising discarding any PVC map of the plurality of PVC maps that includes fewer than a preset number of electrophysiology data points.

15. The method according to claim 11, wherein establishing a plurality of PVC maps, each PVC map of the plurality of PVC maps having an associated PVC template signal, comprises:
  receiving, in the electroanatomical mapping system, user input selecting a plurality of electrophysiology data points, each selected electrophysiology data point including an associated electrophysiological signal; and
  establishing a PVC map for each selected electrophysiology data point,
  wherein the PVC map includes the respective selected electrophysiology data point, and
  wherein the template signal associated with the PVC map is the electrophysiological signal associated with the respective selected electrophysiology data point.

16. The method according to claim 11, wherein establishing a plurality of PVC maps, each PVC map of the plurality of PVC maps having an associated PVC template signal, comprises:
  collecting a plurality of electrophysiology data points using the electroanatomical mapping system;
  identifying a plurality of distinct electrophysiological signal morphologies within the plurality of electrophysiology data points; and
  establishing the plurality of PVC maps using the plurality of distinct electrophysiological signal morphologies.

17. The method according to claim 11, further comprising merging two or more PVC maps of the plurality of PVC maps into a consolidated PVC map.

18. The method according to claim 11, further comprising outputting a graphical representation at least one PVC map of the plurality of PVC maps on a three dimensional cardiac model.

19. A system for mapping premature ventricular contraction ("PVC") activity, comprising:
  a PVC comparison processor configured to:
    compute morphological similarities between an electrophysiological signal associated with an electrophysiology data point and a plurality of PVC template signals; and
    add the electrophysiology data point to a PVC map based upon the computed morphological similarities; and
  a mapping processor configured to generate a graphical representation of the at least one PVC map on a three dimensional cardiac model if the at least one PVC map includes more than a preset number of electrophysiology data points.

* * * * *